United States Patent
Davis et al.

(10) Patent No.: US 10,325,525 B1
(45) Date of Patent: Jun. 18, 2019

(54) COMBINATION WRISTBAND AND LABEL FORM

(71) Applicant: WARD KRAFT, INC., Fort Scott, KS (US)

(72) Inventors: Roger Davis, Garland, KS (US); Gina Staudinger, Louisburg, KS (US); Jesse Crum, Fort Scott, KS (US)

(73) Assignee: Ward Kraft, Inc., Fort Scott, KS (US)

( * ) Notice: Subject to any disclaimer, the term of this patent is extended or adjusted under 35 U.S.C. 154(b) by 115 days.

(21) Appl. No.: 15/676,670

(22) Filed: Aug. 14, 2017

Related U.S. Application Data

(63) Continuation-in-part of application No. 15/180,593, filed on Jun. 13, 2016, now abandoned.

(60) Provisional application No. 62/256,465, filed on Nov. 17, 2015, provisional application No. 62/247,863, filed on Oct. 29, 2015, provisional application No. 62/175,055, filed on Jun. 12, 2015.

(51) Int. Cl.
| | |
|---|---|
| *G09F 3/10* | (2006.01) |
| *A61B 90/90* | (2016.01) |
| *G09F 3/00* | (2006.01) |
| *G09F 3/02* | (2006.01) |
| *A61B 90/96* | (2016.01) |

(52) U.S. Cl.
CPC .............. *G09F 3/005* (2013.01); *A61B 90/90* (2016.02); *G09F 3/0292* (2013.01); *G09F 3/10* (2013.01); *A61B 90/96* (2016.02); *G09F 2003/0201* (2013.01); *G09F 2003/023* (2013.01); *G09F 2003/0226* (2013.01); *G09F 2003/0248* (2013.01)

(58) Field of Classification Search
CPC .......... G09F 3/005; G09F 3/0292; G09F 3/10; G09F 3/0288; G09F 3/04; G09F 3/02; G09F 2003/0201; G09F 2003/0226; G09F 2003/023; G09F 2003/0248; A61B 90/90; A61B 90/96; B32B 7/06; B42D 15/00; B42D 15/08; B42D 15/006; C09J 7/02
See application file for complete search history.

(56) References Cited

U.S. PATENT DOCUMENTS

| | | | |
|---|---|---|---|
| 230,455 A | 7/1880 | Wilcox | |
| 919,983 A | 4/1909 | Walsh | |

(Continued)

FOREIGN PATENT DOCUMENTS

| | | |
|---|---|---|
| DE | 1039431 B | 9/1958 |
| EP | 1974603 A2 | 10/2008 |

(Continued)

*Primary Examiner* — Patricia L. Nordmeyer
(74) *Attorney, Agent, or Firm* — Lathrop Gage L.L.P.

(57) ABSTRACT

A combination wristband and label form has a front ply and a back ply. The front ply has a top portion having a plurality of labels die cut therein and a bottom portion with a generally rectangular wristband configured to receive indicia, and an outer portion surrounding the wristband. The wristband is separable from the form and is formed of a single ply of water-resistant material, and has a first lateral end and a second lateral end. The back ply is at least partially coated in a control bond adhesive and further includes at least one area of silicone. The control bond adhesive includes between about 1 kg and 2 kg of a flexible adhesive; between about 1 kg and 2 kg of water; between about 12 g and 16 g gypsum, and between about 13 g and 23 g fumed silica.

18 Claims, 5 Drawing Sheets

(56) References Cited

U.S. PATENT DOCUMENTS

| | | |
|---|---|---|
| 922,948 A | 5/1909 | Portmore |
| 1,039,431 A | 9/1912 | Moore |
| 1,383,335 A | 7/1921 | Penksa |
| 1,517,456 A | 12/1924 | Pulliam |
| 2,054,227 A | 9/1936 | Nichols |
| 2,073,280 A | 3/1937 | Lederer |
| 2,553,676 A | 5/1951 | Roos |
| 2,641,074 A | 6/1953 | Richmond |
| 2,687,978 A | 8/1954 | Vogt |
| 2,914,166 A | 11/1959 | Bihler |
| 3,153,869 A | 10/1964 | Twentier |
| 3,197,899 A | 8/1965 | Twentier |
| 3,402,808 A | 9/1968 | Yannuzzi |
| 3,517,802 A | 6/1970 | Petrie |
| 3,585,743 A | 6/1971 | Jeffers |
| 3,660,916 A | 5/1972 | McDermott et al. |
| 3,854,229 A | 12/1974 | Morgan |
| 4,004,362 A | 1/1977 | Barbieri |
| 4,078,324 A | 3/1978 | Wiebe |
| 4,138,234 A | 2/1979 | Kubesa |
| 4,179,833 A | 12/1979 | Knodel |
| 4,226,036 A | 10/1980 | Krug |
| 4,233,715 A | 11/1980 | McDermott |
| 4,314,415 A | 2/1982 | De Woskin |
| 4,318,234 A | 3/1982 | Charles et al. |
| 4,370,370 A | 1/1983 | Iwata et al. |
| 4,565,731 A | 1/1986 | Komatsu et al. |
| 4,612,718 A | 9/1986 | Golub et al. |
| 4,627,994 A | 12/1986 | Welsch |
| 4,630,384 A | 12/1986 | Breen |
| 4,682,431 A | 7/1987 | Kowalchuk |
| 4,696,843 A | 9/1987 | Schmidt |
| 4,783,917 A | 11/1988 | Smith et al. |
| 4,829,604 A | 5/1989 | Allen et al. |
| 4,854,610 A | 8/1989 | Kwiatek |
| 4,855,277 A | 8/1989 | Walter |
| 4,914,843 A | 4/1990 | Dewoskin |
| 4,941,210 A | 7/1990 | Konucik |
| 4,950,638 A | 8/1990 | Yuyama et al. |
| 4,956,931 A | 9/1990 | Selke et al. |
| D312,654 S | 12/1990 | Giordano |
| 4,978,144 A | 12/1990 | Schmidt et al. |
| 4,991,337 A | 2/1991 | Solon |
| RE33,616 E | 6/1991 | Welsch |
| 5,026,084 A | 6/1991 | Pasfield |
| 5,045,426 A | 9/1991 | Maierson et al. |
| 5,048,870 A | 9/1991 | Mangini et al. |
| 5,135,789 A | 8/1992 | Schmidt |
| 5,222,823 A | 6/1993 | Conforti |
| 5,227,004 A | 7/1993 | Belger |
| 5,227,209 A | 7/1993 | Garland |
| 5,283,969 A | 2/1994 | Weiss |
| 5,311,689 A | 5/1994 | Lindsey |
| 5,318,326 A | 6/1994 | Garrison |
| 5,331,140 A | 7/1994 | Stephany |
| 5,351,993 A | 10/1994 | Wright et al. |
| 5,364,133 A | 11/1994 | Hofer et al. |
| 5,370,420 A | 12/1994 | Khatib et al. |
| 5,381,617 A | 1/1995 | Schwartztol et al. |
| 5,383,686 A | 1/1995 | Laurash |
| 5,395,667 A | 3/1995 | Ohno et al. |
| 5,401,110 A | 3/1995 | Neeley |
| 5,418,026 A | 5/1995 | Dronzek, Jr. et al. |
| 5,421,942 A | 6/1995 | Hoffmann |
| 5,423,574 A | 6/1995 | Forte-Pathroff |
| 5,427,416 A | 6/1995 | Birch |
| 5,448,846 A | 9/1995 | Peterson et al. |
| 5,457,906 A | 10/1995 | Mosher, Jr. |
| 5,486,021 A | 1/1996 | Laurash |
| 5,486,436 A | 1/1996 | Lakes |
| 5,509,693 A | 4/1996 | Kohls |
| 5,509,694 A | 4/1996 | Laurash et al. |
| 5,518,787 A | 5/1996 | Konkol |
| 5,524,934 A | 6/1996 | Schwan |
| 5,547,227 A | 8/1996 | Laurash et al. |
| 5,560,657 A | 10/1996 | Morgan |
| 5,562,789 A | 10/1996 | Hoffmann |
| 5,581,924 A | 12/1996 | Peterson |
| 5,586,788 A | 12/1996 | Laurash |
| 5,595,404 A | 1/1997 | Skees |
| 5,596,202 A | 1/1997 | Arakawa |
| 5,598,970 A | 2/1997 | Mudry et al. |
| 5,601,222 A | 2/1997 | Haddad |
| 5,601,313 A | 2/1997 | Konkol et al. |
| 5,630,627 A | 5/1997 | Stewart |
| 5,637,369 A | 6/1997 | Stewart |
| 5,648,143 A | 7/1997 | Mehta et al. |
| 5,653,472 A | 8/1997 | Huddleston et al. |
| 5,662,976 A | 9/1997 | Popat et al. |
| 5,670,015 A | 9/1997 | Finestone et al. |
| 5,687,903 A | 11/1997 | Akridge et al. |
| 5,721,178 A | 2/1998 | Lalande |
| D391,991 S | 3/1998 | Conner |
| 5,752,722 A | 5/1998 | Moore et al. |
| 5,765,885 A | 6/1998 | Netto |
| 5,785,354 A | 7/1998 | Haas |
| 5,837,337 A | 11/1998 | Schnitzer |
| 5,837,341 A | 11/1998 | Johnstone |
| 5,840,143 A | 11/1998 | Swanson |
| 5,842,722 A | 12/1998 | Carlson |
| 5,877,742 A | 3/1999 | Klink |
| 5,933,993 A | 8/1999 | Riley |
| 5,984,363 A | 11/1999 | Dotson et al. |
| 6,000,160 A | 12/1999 | Riley |
| 6,006,460 A | 12/1999 | Blackmer |
| D423,044 S | 4/2000 | Burke et al. |
| 6,053,535 A | 4/2000 | Washburn et al. |
| 6,055,756 A | 5/2000 | Aoki |
| 6,058,639 A | 5/2000 | Tinklenberg et al. |
| 6,067,739 A | 5/2000 | Riley |
| 6,071,585 A | 6/2000 | Roth |
| 6,092,321 A | 7/2000 | Cheng |
| 6,108,876 A | 8/2000 | Hubbert |
| 6,155,476 A | 12/2000 | Fabel |
| 6,155,603 A | 12/2000 | Fox |
| 6,159,570 A | 12/2000 | Ulrich et al. |
| 6,199,730 B1 | 3/2001 | Chisolm |
| D44,804 S | 9/2001 | Hamilton et al. |
| 6,303,539 B1 | 10/2001 | Kosarew |
| 6,331,018 B1 | 12/2001 | Roth et al. |
| 6,343,819 B1 | 2/2002 | Shiozaki |
| 6,361,078 B1 | 3/2002 | Chess |
| 6,364,366 B1 | 4/2002 | Schwartz |
| 6,409,871 B1 | 6/2002 | Washburn et al. |
| 6,438,881 B1 | 8/2002 | Riley |
| 6,510,634 B1 | 1/2003 | Riley |
| 6,517,921 B2 | 2/2003 | Ulrich et al. |
| D473,264 S | 4/2003 | Sanford et al. |
| 6,611,962 B2 | 9/2003 | Redwood et al. |
| 6,641,048 B1 | 11/2003 | Schintz et al. |
| 6,685,228 B2 | 2/2004 | Riley |
| 6,748,687 B2 | 6/2004 | Riley |
| 6,782,648 B1 | 8/2004 | Mosher, Jr. |
| 6,807,680 B2 | 10/2004 | Sloot |
| 6,836,215 B1 | 12/2004 | Laurash et al. |
| 6,844,041 B2 | 1/2005 | Squier et al. |
| D503,197 S | 3/2005 | Stewart et al. |
| 6,863,311 B2 | 3/2005 | Riley |
| 6,971,200 B2 | 12/2005 | Valenti, Jr. |
| 6,981,948 B2 | 1/2006 | Pellegrino et al. |
| 7,017,293 B2 | 3/2006 | Riley |
| 7,017,294 B2 | 3/2006 | Riley |
| D521,565 S | 5/2006 | Stewart |
| 7,047,682 B2 | 5/2006 | Riley |
| 7,197,842 B2 | 4/2007 | Ali |
| 7,222,448 B2 | 5/2007 | Riley |
| 7,240,446 B2 | 7/2007 | Bekker |
| 7,286,055 B2 | 10/2007 | Girvin et al. |
| 7,523,576 B1 | 4/2009 | Petty |
| D611,984 S | 3/2010 | Ali et al. |
| 7,763,344 B2 | 7/2010 | Riley et al. |
| 7,779,569 B2 | 8/2010 | Riley et al. |
| 7,779,570 B2 | 8/2010 | Riley |
| 7,784,209 B2 | 8/2010 | Greer |

(56) References Cited

U.S. PATENT DOCUMENTS

| | | |
|---|---|---|
| 7,784,210 B2 | 8/2010 | Riley et al. |
| 7,818,908 B2 | 10/2010 | Greer |
| 7,823,310 B2 | 11/2010 | Jain et al. |
| 7,877,915 B2 | 2/2011 | Jain et al. |
| 7,883,018 B2 | 2/2011 | Riley et al. |
| 7,918,045 B2 | 4/2011 | Riley |
| 8,011,125 B2 | 9/2011 | Riley et al. |
| 2002/0152928 A1 | 10/2002 | Lawandy et al. |
| 2002/0176973 A1 | 11/2002 | Keiser |
| 2003/0001381 A1 | 1/2003 | Riley |
| 2003/0003249 A1 | 1/2003 | Benim et al. |
| 2003/0011190 A1 | 1/2003 | Ryan |
| 2004/0060216 A1 | 4/2004 | Riley |
| 2004/0068906 A1 | 4/2004 | Riley |
| 2004/0128892 A1 | 7/2004 | Valenti, Jr. |
| 2004/0148836 A1 | 8/2004 | Riley |
| 2004/0244251 A1 | 12/2004 | Riley |
| 2005/0091896 A1 | 5/2005 | Kotik et al. |
| 2005/0108912 A1 | 5/2005 | Bekker |
| 2005/0279001 A1 | 12/2005 | Riley |
| 2005/0281989 A1 | 12/2005 | Finger |
| 2006/0230661 A1 | 10/2006 | Bekker |
| 2006/0236578 A1 | 10/2006 | Saint et al. |
| 2006/0242875 A1 | 11/2006 | Wilson et al. |
| 2006/0261958 A1 | 11/2006 | Klein |
| 2007/0089342 A1 | 4/2007 | Jain et al. |
| 2007/0120358 A1 | 5/2007 | Waggoner et al. |
| 2007/0243361 A1 | 10/2007 | Riley et al. |
| 2007/0257113 A1 | 11/2007 | Davis et al. |
| 2008/0098636 A1 | 5/2008 | Greer |
| 2009/0031602 A1 | 2/2009 | Riley |
| 2009/0094872 A1 | 4/2009 | Ali et al. |
| 2009/0094873 A1 | 4/2009 | Riley |
| 2009/0193701 A1 | 8/2009 | Greer |
| 2009/0277061 A1 | 11/2009 | Jain et al. |
| 2009/0282717 A1 | 11/2009 | Jain et al. |
| 2010/0071241 A1 | 3/2010 | Jain et al. |
| 2010/0253060 A1 | 10/2010 | Riley et al. |
| 2010/0281724 A1 | 11/2010 | Greer et al. |
| 2011/0042933 A1 | 2/2011 | Landsman et al. |
| 2012/0210620 A1 | 8/2012 | Jain et al. |
| 2013/0056974 A1 | 3/2013 | Jain et al. |
| 2016/0335928 A1* | 11/2016 | Lux .................. G09F 3/02 |

FOREIGN PATENT DOCUMENTS

| | | |
|---|---|---|
| EP | 2806594 A1 | 11/2014 |
| FR | 960859 A | 4/1950 |
| GB | 561777 A | 6/1944 |
| GB | 2045718 A | 11/1980 |
| GB | 2160492 A | 12/1985 |
| GB | 2228915 A | 9/1990 |
| JP | 08190350 A | 7/1996 |
| JP | 08299035 A | 11/1996 |
| JP | 3032299 U | 12/1996 |
| JP | 10207374 A | 8/1998 |
| JP | 11015383 A | 1/1999 |
| JP | 2001316921 A | 11/2001 |
| JP | 2002117190 A | 4/2002 |
| JP | 2002351321 A | 12/2002 |
| JP | 2003066849 A | 3/2003 |
| JP | 2003157010 A | 5/2003 |
| JP | 2003164307 A | 6/2003 |
| JP | 2006039209 A | 2/2006 |
| WO | 9612618 A1 | 5/1996 |
| WO | 9823081 A1 | 5/1998 |
| WO | 9918817 A1 | 4/1999 |
| WO | 0239412 A2 | 5/2002 |
| WO | 03003331 A2 | 1/2003 |
| WO | 2004028826 A2 | 4/2004 |
| WO | 2005064574 A1 | 7/2005 |
| WO | 2006007356 A1 | 1/2006 |
| WO | 2007021375 A2 | 2/2007 |
| WO | 2007133906 A2 | 11/2007 |
| WO | 2008079952 A2 | 7/2008 |
| WO | 2009099787 A1 | 8/2009 |
| WO | 2009137195 A1 | 11/2009 |
| WO | 2010129131 A1 | 11/2010 |

* cited by examiner

COMBINATION WRISTBAND AND LABEL FORM

RELATED APPLICATIONS

This application is a continuation-in-part of U.S. patent application Ser. No. 15/180,593, filed Jun. 13, 2016, which is pending. U.S. patent application Ser. No. 15/180,593 claims priority to U.S. Provisional Application No. 62/175,055, filed on Jun. 12, 2015, U.S. Provisional Application No. 62/247,863, filed on Oct. 29, 2015, and U.S. Provisional Application No. 62/256,465, filed on Nov. 17, 2015. Each of the disclosures re incorporated by reference in their entireties herein.

BACKGROUND

The wristband is a frequently-used instrument for distinguishing among various groups of people. For example, wristbands may be used to identify persons in short term healthcare facilities, or to distinguish between levels of access (e.g., at a concert) or permissions. Thus, there is a significant market for wristbands. Wristbands with improved performance capabilities are desirable.

Many wristband designs require multiple steps to remove the wristband from its liner and subsequently affix it to the wearer. For example, the user may be required to remove the liner in order to expose adhesive, or to fold a part of the wristband over the face portion in order to secure the wristband in place. Some wristbands include adhesive on both ends thereof, which may make it difficult for the user to affix the wristband without attaching the adhesive to unattended areas. Additionally, this may make it difficult to remove the wristband when desired.

SUMMARY

The following presents a simplified summary of the invention in order to provide a basic understanding of some aspects of the invention. This summary is not an extensive overview of the invention. It is not intended to identify critical elements of the invention or to limit the scope of the invention. Its sole purpose is to present some concepts of the invention in a simplified form as a prelude to the more detailed description presented below.

According to an embodiment, a combination wristband and label form comprises a top portion and a bottom portion. The top portion has a plurality of labels die cut therein. The bottom portion has a rectangular wristband configured to receive an indicia, and an outer portion surrounding the wristband. The wristband is separable from the form and is formed of a single ply of water-resistant material. The wristband has a first lateral end and a second lateral end. The first lateral end has an adhesive area comprising adhesive adjacent the first lateral end. The second lateral end comprises perforations. There is no adhesive on the wristband outside the adhesive area. The form further comprises a release liner having a release material. Removal of the wristband from the form exposes a first area of the release liner. The first area is devoid of a void space. The outer portion is permanently secured to the release liner.

According to another embodiment, a combination wristband and label form comprises a top portion and a bottom portion. The top portion has a plurality of labels die cut therein. Each of the labels is configured to be removable from the form. The bottom portion has a wristband configured to receive an indicia, and an outer portion surrounding the wristband. The wristband is separable from the form and is formed of a single ply of water-resistant and tamper-resistant material. The wristband has a first lateral end and a second lateral end. The first lateral end has an adhesive area comprising adhesive adjacent the first lateral end. The second lateral end comprises perforations. The form includes a release liner having a release material. Removal of the wristband from the form exposes a first area of the release liner. The form is configured for multiple passes through a printer after the wristband is removed therefrom.

In still another embodiment, a combination wristband and label form has a front ply and a back ply. The front ply has a top portion having a plurality of labels die cut therein and a bottom portion with a generally rectangular wristband configured to receive indicia, and an outer portion surrounding the wristband. The wristband is separable from the form and is formed of a single ply of water-resistant material, and has a first lateral end and a second lateral end. The back ply is at least partially coated in a control bond adhesive and further includes at least one area of silicone. The control bond adhesive includes between about 1 kg and 2 kg of a flexible adhesive; between about 1 kg and 2 kg of water; between about 12 g and 16 g gypsum, and between about 13 g and 23 g fumed silica. The control bond adhesive maintains the wristband in temporary contact with the back ply between the first lateral end and the second lateral end, and removal of the wristband exposes a first area of the back ply such that the first area is devoid of a void space. The outer portion is permanently sealed to the back ply.

In a further embodiment, a combination wristband and label form includes a front ply comprising at least one wristband; and a back ply at least partially coated in a control bond adhesive. The control bond adhesive is a mixture comprising between about 3 pounds and 4 pounds of a flexible adhesive; between about 2 pounds and 3 pounds of soft water; between about 1 tsp and 2 tsp gypsum, and between about 19 and 22 tsp fumed silica. The control bond adhesive maintains the wristband in temporary contact with the back ply.

In still yet another embodiment a method of forming a combination wristband and label form, includes the steps of (1) providing a front ply comprising a generally rectangular wristband configured to receive an indicia, and an outer portion surrounding the wristband; (2) providing a back ply; (3) applying a control bond adhesive to the back ply at a first area; (4) applying silicone to the back ply at a second area; and (5) securing the front ply to the back ply such that the wristband mates with the back ply at the first area. The wristband is separable from the form and is formed of a single ply of water-resistant material, and has a first lateral end and a second lateral end. The control bond adhesive comprises between about 1 kg and 2 kg of a flexible adhesive; between about 1 kg and 2 kg of water; between about 12 g and 16 g gypsum, and between about 13 g and 23 g fumed silica. The control bond adhesive maintains the wristband in temporary contact with the back ply; and the outer portion is permanently sealed to the back ply.

DETAILED DESCRIPTION

Many wristband designs require multiple steps in order to remove the wristband from its liner and subsequently affix it to the wearer. For example, the user may be required to remove the liner in order to expose adhesive, or to fold a part of the wristband over the face portion in order to secure the wristband in place. Some wristbands include adhesive on both ends, which may make it difficult for the user to affix the wristband without attaching the adhesive to unattended areas. Additionally, this may make it difficult to remove the wristband when desired.

Other wristbands may include two layers of material, fastened together with adhesive. Here, the wristband is usually thicker and heavier. Still further designs include a paper layer which is not water resistant that tends to get torn and tattered. According to these designs, a wristband portion is permanently adhered to a paper backing sheet which is die cut in a form, to form a two-layer wristband. The wristband, consisting of the backing layer and the wristband portion, is removed from the form leaving a wristband-shaped hole in the form. This may be undesirable, because the holes in the form may prevent the form from being able to pass through a printer multiple times.

One embodiment of the present invention, described in detail herein, provides for a wristband which may be removed from a form via one generally continuous motion, and which, upon removal, may be conveniently secured to a wearer as-is. The wristband may be configured to include only a single layer of a light, synthetic (or other similar) material, thus making the wristband approximately half of the thickness of traditional wristbands currently on the market. Finally, the synthetic material may be water and tear resistant such that the wristband will not tear when removed from the backing sheet prior to affixing the wristband to the person. The wristband may be configured to be removed from a form without leaving a hole in the form, thus leaving the backing sheet intact such that the form may be passed through a printer multiple times.

Figure 1:
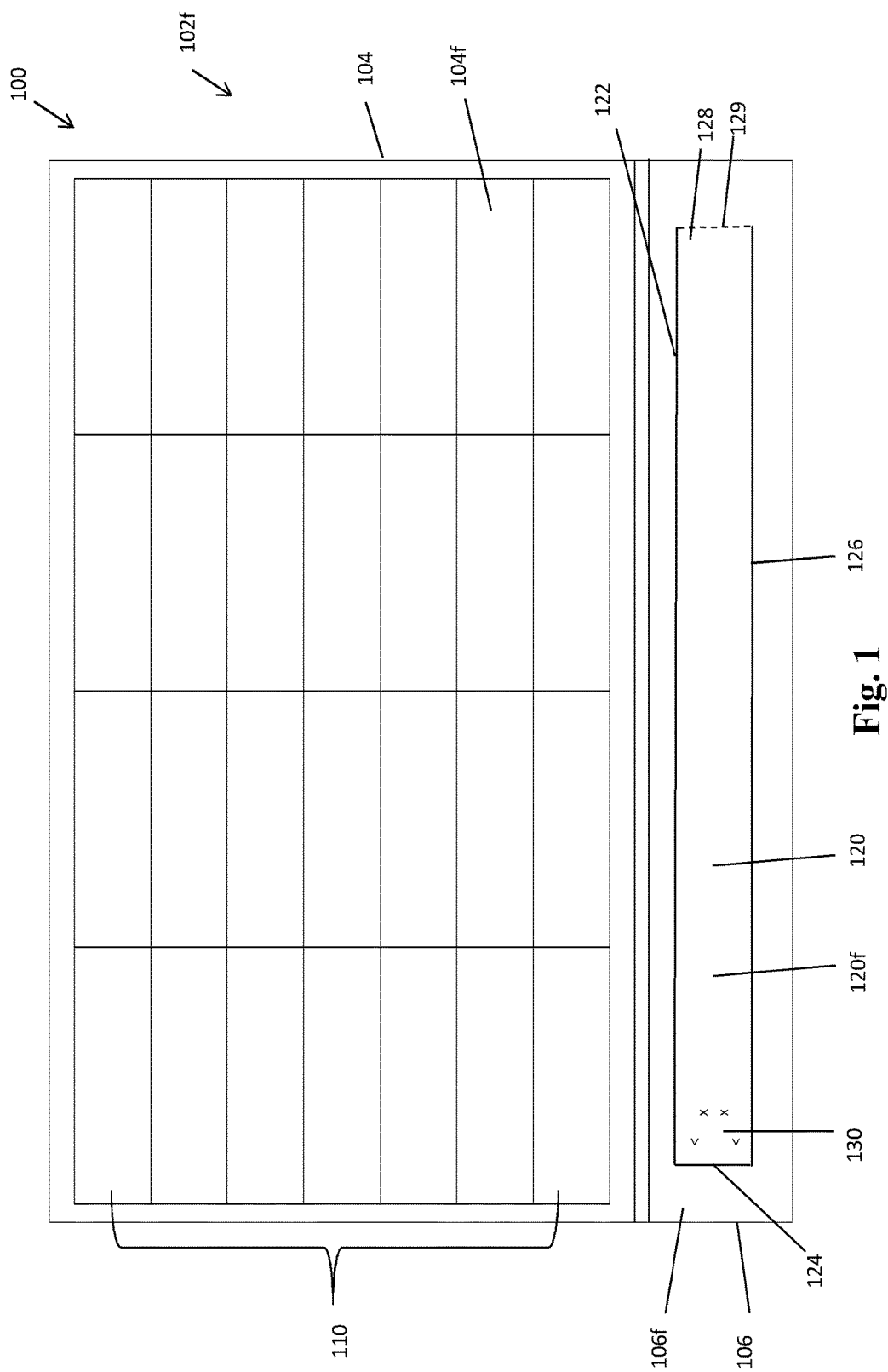
FIG. 1 is a front side view of a combination wristband and label form according to one embodiment of the invention.

With reference now to the figures, FIG. 1 shows a combination wristband and label form 100 according to one embodiment of the invention. The form 100 includes a front sheet 102 adhered to a backing sheet 140. The front sheet 102 has a front side 102*f* and a back side 102*b*. The front sheet 102 may in some embodiments be separated into a top portion 104 and a bottom portion 106 having a relatively small gap therebetween. The top portion 104 and the bottom portion 106 may each have a front face 104*f* and 106*f*, respectively.

The front surface 104*f* of the top portion 104 may include a plurality of labels 110. The labels 110 may be arranged in columns and rows, for example, 4×6. However, the labels 110 may be provided in any combinations of columns (e.g., 1, 2, 3, 4, etc.) and rows (e.g., 1, 2, 3, 4, etc.). The labels 110 may be configured to receive indicia. Accordingly, the front surface 104*f* may be constructed of paper or other appropriate textile sufficient for receiving ink, e.g., from a printer or other marking device.

The labels 110 may have a variety of constructions. For example, the figures illustrate the labels 110 as having a generally rectangular configuration. However, the labels 110 may be square, circular, polygonal, etc. Additionally, a combination of label configurations may be employed on a single form 100.

The bottom portion 106 may comprise one or more wristbands 120. The wristbands 120 may be configured to be printable. In some embodiments, the form 100 may be configured to be passed through a printer so that indicia (e.g., patient name, patient medications, machine readable information such as barcodes, et cetera) may be printed directly on the wristband 120.

The wristband 120 may be defined by two longitudinally opposing sides (or ends) 122 and 126, which may be die cut into the bottom portion front face 106*f*, and two laterally opposing sides (or ends) 124 and 128. One of the laterally opposed sides, e.g., side 128, may include perforations 129. Optionally, one or more of the laterally opposed sides, e.g., side 124 and/or 128, may contain an area of adhesive 132 (FIG. 2) on a backside 120*b* of the wristband 120. The adhesive 132 may keep the end 124 secured to the backing sheet 140 as described below. The wristband 120 may be substantially held into position via the adhesive patch 132 and the perforated side 128. The wristband 120 may contain no adhesive apart from the adhesive 132 adjacent the end 124.

In another embodiment, the wristband backside 120*b* and/or the backing sheet 143 may be coated with a control bond chemical (or release bond agent). Traditionally, dry adhesives are used and require the application of two or more layers in order to achieve the desired results. For example, for the dry adhesive to work correctly, a release coating must first be applied to one ply, and another coating that provides for temporary adhesion with the first ply must be applied to the other ply. Additional layers of coating may be further required. Here, the release bond agent is configured such that only a single layer is required, thus making the application quicker, easier, and less expensive, and the thickness of the wristband can be reduced.

In one embodiment, the release coating comprises an effective amount of a flexible adhesive, water, sulfates, silica, and optionally, pigment. The flexible adhesive may be any adhesive that is flexible when dry. Preferably, the adhesive is a water-based adhesive, such as a product from the line of Swift®Tak adhesives. In an embodiment, the adhesive is a desirable Swift®Tak adhesive (e.g., Swift®Tak 48572). In order for the release coating to achieve its desired function, the water in the mixture may preferably be soft water. Soft water may be naturally occurring, and is classified by the low amount of dissolved minerals found therein. In many cases, hard water may be softened using a filtration technique. In one embodiment, the water used in the release coating mixture is softened via treatments of the water with activated coconut coir, or activated charcoal from coconut husk (ACC). Other water treatment methods may alternately, or additionally, be utilized, including but not limited to reverse osmosis, activated carbon, etc.

In embodiments, the sulfate is calcium sulfate ($CaSO_4$). The calcium sulfate may be helpful for bringing together the components of the mixture. The silica may be fumed silica, which is added as a thickening agent. Finally, the pigment, which may optionally be included as part of the release coating mixture, may desirably be water based. The pigment may be added such that a user can see where the release coating is applied in real time. In embodiments, the pigment may disappear as the coating cures such that it does not undesirably change the aesthetics of the final product.

The adhesive to water ratio may be about 60:40, preferably 55:45, and most preferably about 56:44. In one embodiment, the composition comprises about 4 pounds of adhesive and about 3 pounds of water. In another embodiment, the amount of adhesive is between about 3 and 4 pounds, and the amount of water is between about 2 and 3 pounds. For example, the amount of adhesive may be about 3.6 pounds, and the amount of water may be about 2.8 pounds.

In embodiments, it may be preferable to increase the degree of adhesion. Here, the ratio of adhesive to water may be adjusted such that the amount of adhesive is increased and the amount of water is decreased.

The measurable weight of calcium sulfate (gypsum) and fumed silica may be substantially smaller than the amount of adhesive and water. Accordingly, it may be preferable to measure the amount of gypsum and fumed silica in terms of volume. In one embodiment, about 1 teaspoon of gypsum is provided as part of the composition. The amount of fumed silica is about 20 teaspoons. In another embodiment, the amount of gypsum is between about 1 and 2 teaspoons, and the amount of fumed silica is between about 19 and 25 teaspoons. In still another embodiment, the amount of gypsum is about 1.3 teaspoons, and the amount of fumed silica is about 19 heaping teaspoons.

In still another embodiment, the amount of adhesive is between about 1 and 2 kg (1000 g and 2000 g), preferably between about 1.4 and 1.8 kg, and most preferably about 1.6 kg (about 1632 g). The amount of water is between about 1 and 2 kg (1000 g and 1500 g), preferably between about 1.1 kg and 1.3 kg, and most preferably about 1.3 kg (about 1270 g). The amount of gypsum is between about 12 and 16 g, preferably between about 13 and 15 g, and most preferably about 14.87 g. Finally the amount of fumed silica ranges from about 13 g to about 24 g, preferably from about 15 g to 22 g, and most preferably about 16 g.

Optionally, an amount of pigment is provided along with the adhesive, water, gypsum, and fumed silica. The amount of pigment may be just enough so that the composition has a tint, or color, and may be based on the preferences of the user.

The components of the composition may be blended together with a cutting blade to ensure the materials are adequately combined. Other mixing apparatus and methods known to those of skill in the art may be utilized for mixing together the components.

When mixed, the composition may have a viscosity close to that of water. In other words, the composition may have a low viscosity such that it may be easily applied to the combined wristband and label form as described herein. In embodiments of higher amounts of adhesive, the viscosity may additionally be higher.

The control bond adhesive composition may be applied to the combined wristband and label form according to methods known to those of skill in the art. Using a roll-coater device, the adhesive may be applied to the backing in the area of the wristband. The adhesive may be applied in a pattern. The pattern may be configured such that removal of the wristband provides the user with a "zipper" effect—the user may hear a noise similar to that heard during operation of a zipper, and further feel as if the wristband were being unzipped from the backing.

The wristband ply (e.g., the front sheet 102) may then be mated with the backing sheet 140. The paper side (e.g., backing sheet 140) may be heated up, causing the pores of the paper to expand. The control bond adhesive therefore dries within the pores of the paper, resulting in a desirable temporary control bond.

The wristband 120 may be generally rectangular, as shown. Alternatively, the wristband 120 may take on other desirable shapes. In one embodiment, a height of the adhesive end (e.g., end 124) may be less than a height of the remainder of the wristband 120 (including being less than the height of the end 128).

The wristband 120 may be further equipped with security slits 130. The security slits 130 may be configured to tear, should the wristband 120 be tampered with after the wristband 120 is applied to a wearer. This may be beneficial to ensure that the wristband 120 remains associated with the intended wearer, particularly in a healthcare environment where the wristband 120 includes patient-specific information.

The bottom portion 106 (including the wristband 120) may be constructed of a synthetic material, such as polyester fabric or plastic, for example. Other materials may additionally, or alternately, be appropriate. Those of skill in the art may recognize that it may be beneficial for the wristband 120 material to be resistant to water or other liquid, which may cause the integrity of the wristband 120 to be prematurely compromised.

Figure 2:
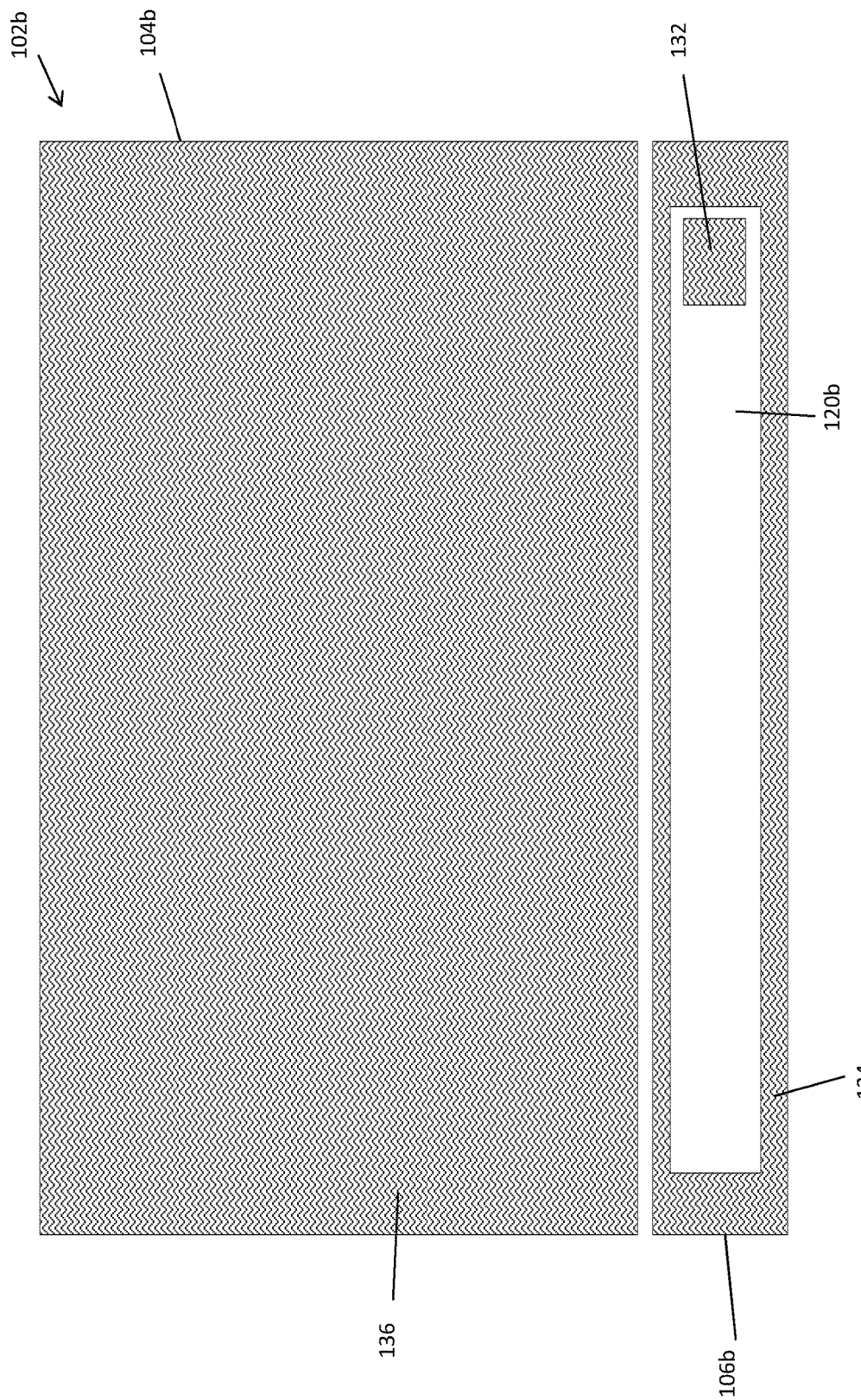
FIG. 2 is a back side view of the combination wristband and label form according to the embodiment of FIG. 1.

Attention is now directed to FIG. 2, which shows an embodiment of the back side 102b of the form 100. The back side 102b may include a back face 104b of the top portion 104 and a back face 106b of the bottom portion 106. The back face 104b of the top portion 104 may include an adhesive area 136. The adhesive area 136 may allow for the labels 110 to be releasably secured to the backing sheet 140. The back face 106b of the bottom portion 106 may additionally have adhesive areas 132, described above, and 134. The adhesive area 134 may correspond to the area surrounding the wristband 120 which remains in place when the wristband 120 is removed from the form 100.

Figure 3:
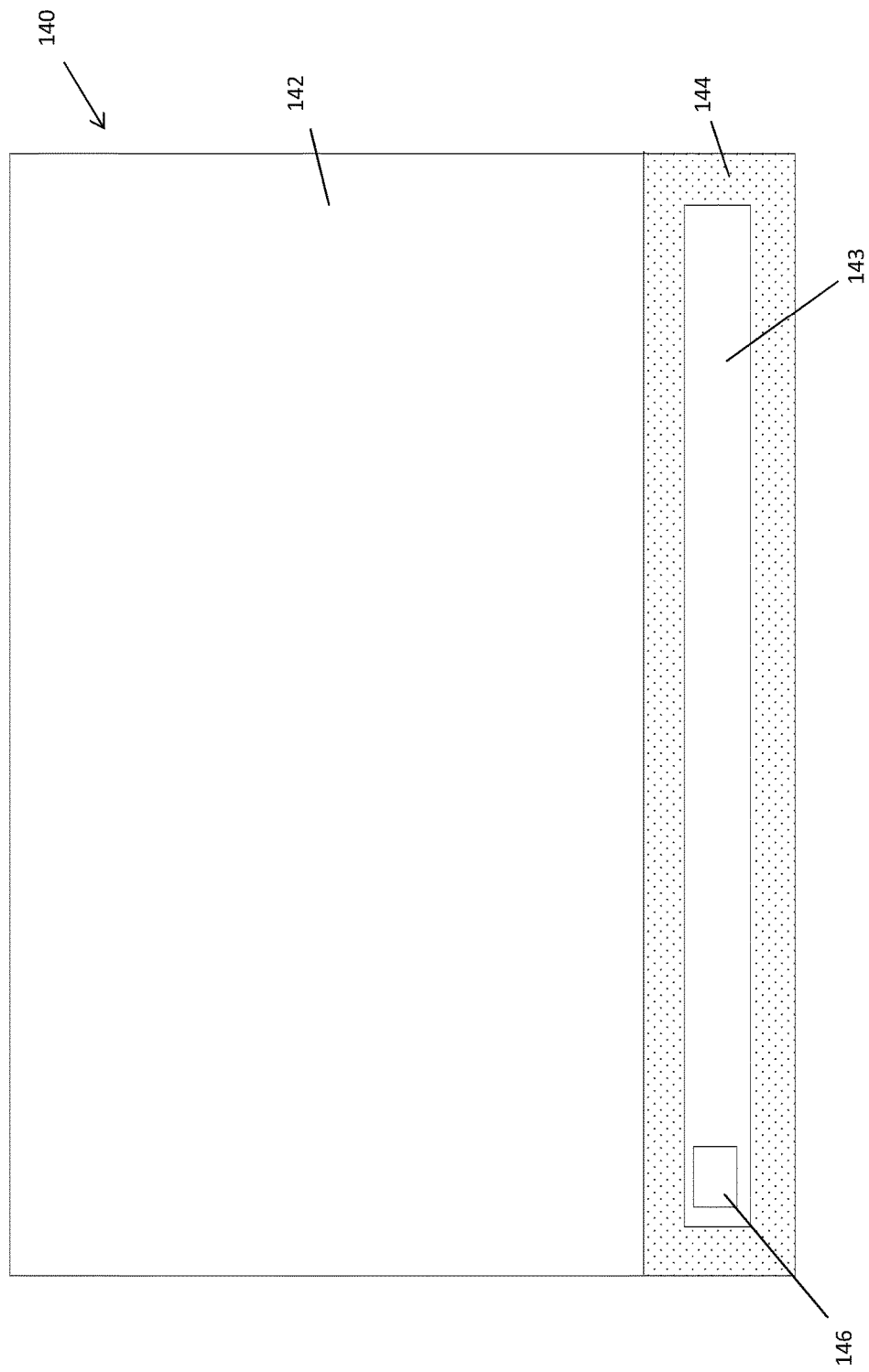
FIG. 3 is a front view of a backing sheet that is attached to a back side of the form of FIG. 1.

The adhesive areas 132, 134, and 136 of the back faces 104b and 106b may adhere to the backing sheet 140, illustrated in FIG. 3. In certain embodiments, the backing sheet 140 may be constructed of paper or a synthetic resin, and may include a layer of silicone (or another similar release material) in the areas corresponding to the adhesive areas 132, 134, and 136. For example, the adhesive area 136 may releasably adhere to the silicone material 142, adhesive area 132 may releasably adhere to silicone material 146, and adhesive area 134 may adhere to silicone material 144. The silicone material 144 may be applied in a pattern. The patterned silicone 144 may allow for a more permanent adhesion between the backing sheet 140 and the front sheet 102 in areas void of silicone (e.g., the bond between the area of the bottom portion 106 surrounding the wristband 120 and the backing sheet 140 may be stronger than the bond between the top portion 104 and the backing sheet). This may keep the area of the bottom portion 106 surrounding the wristband 120 in place on the backing sheet 140. In some embodiments, the silicone material 144 may be omitted so that the area of the bottom portion 106 surrounding the wristband 120 permanently adheres to the backing sheet 140. In embodiments, one or more adhesive areas (e.g., the adhesive area 132, 134, 136, etc.) may not be present, thus reducing the need for silicone on the backing sheet 140.

When the wristband 120 is removed from the form 100, the area 143 of the backing sheet 140 behind the wristband 120 may remain intact. Such may provide several benefits over prior art wristbands. For example, as noted above, prior art methods consisting of "punching out" the wristband from the form leaves a void that may prevent the rest of the form from being used at a later time. However, if the form remains intact, as in the present invention, it may be used multiple times, for example, to print on the labels 110. This may be beneficial because it is often desirable to print the labels 110 at different times (for example, it may be desirable to print new labels 110 to reflect changes made to medications prescribed to a patient during the course of his treatment). A new label 110, such as a label 110 leftover on the form 100, may thus be printed with the new information until all the labels 110 have been used. Of course, the labels 110 may be used for any desirable purposes, such as for labeling patient files and other documents, vials, etc. The labels 110 may all be printed with information in a single pass through the printer, or the form 100 may be passed through the printer multiple times such that the labels 110 are printed as needed.

According to one embodiment, in use, after the wristband 120 has been printed, the user may peel the side (e.g., side 124) of the wristband 120 up and away from the form 100, inserting his or her finger under the wristband side 126 until the finger exits at side 122. The user may then tear the side 128 along the perforations 129 to free the wristband 120 from the form 100. Alternately, the user may hold the wristband 100, e.g., from side 122 or 126, between his index finger and thumb, tear the side 128 along the perforations 129, and then separate the wristband 120, including the side 124 having the adhesive 132, from the form 100. In this way, the user may remove the wristband 120 from the form 100 in one generally continuous motion. The user may then attach the wristband 120 to a person's wrist by wrapping the wristband 120 around the wrist, face up, and fastening the adhesive end (e.g., side 124) to the face of the wristband 120. Such quick and convenient removal of the wristband 120 from the form 100 and its ready securement to a person's wrist may be preferable, as compared for example, to wristbands that must be removed from the associated forms in several steps or which need to be folded or otherwise reconfigured after they have been removed from the form and before they are secured to a wearer's wrist.

In another embodiment, wherein wristband 120 is secured to the backing sheet 140 via the control bond adhesive, the user may peel back one side (e.g., side 124) and remove the wristband 120 by pulling the wristband 120 away from the backing sheet 140. As described above, the control bond adhesive may provide an enhanced experience to the user, allowing the user to hear and feel the removal of the wristband 120 from the backing sheet 140.

Figure 4:
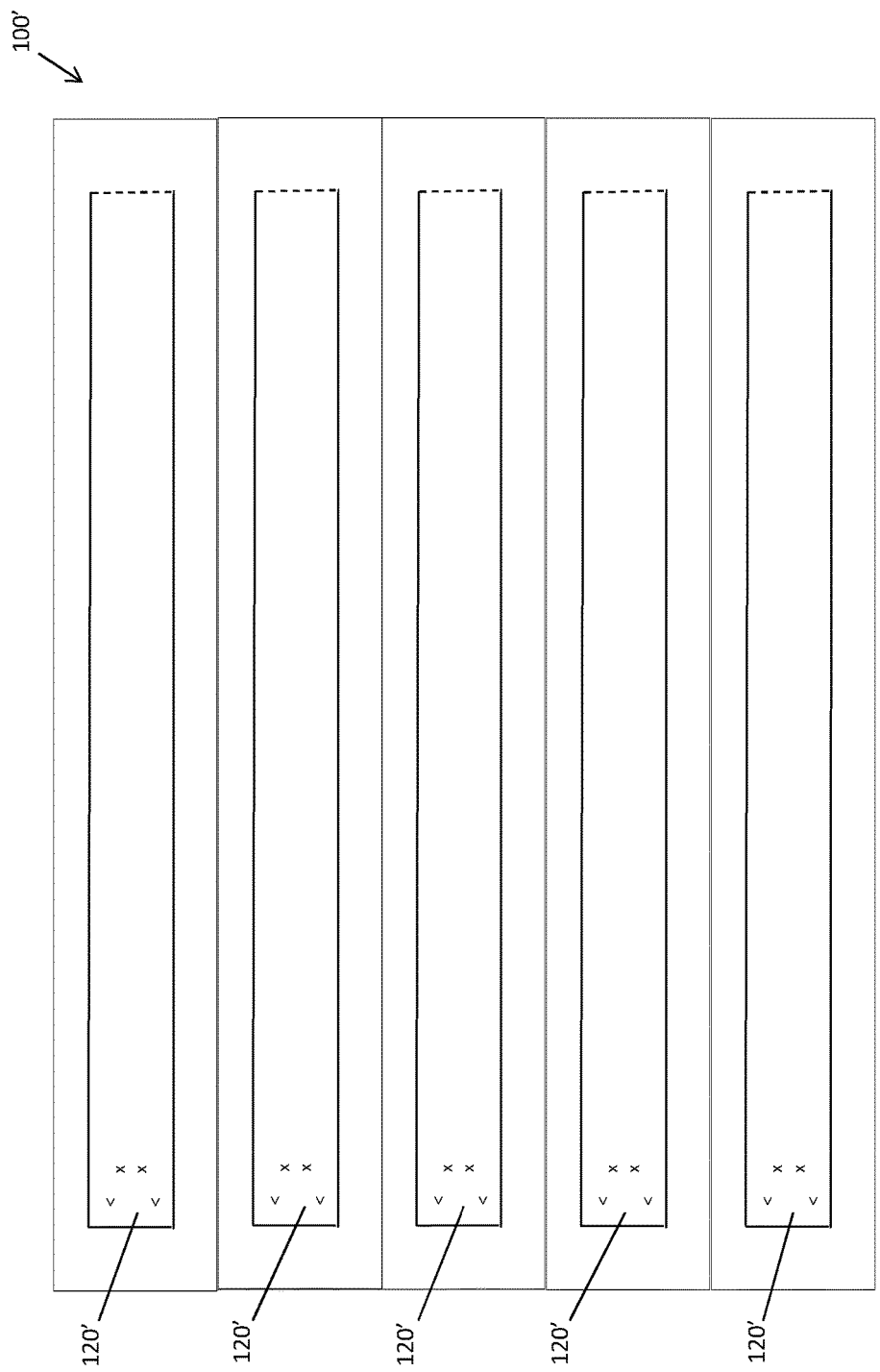
FIG. 4 is a front side view of an alternative embodiment of the form of FIG. 1.
Figure 5:
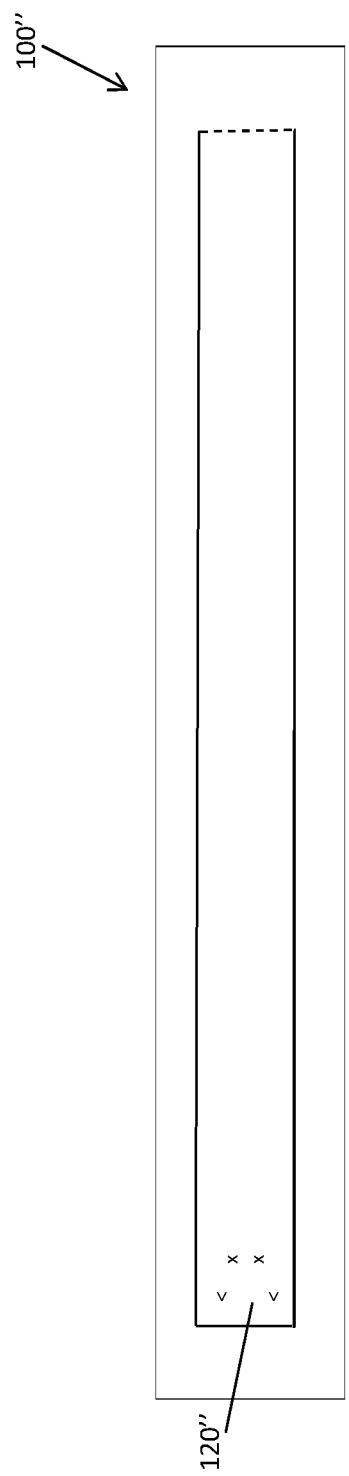
FIG. 5 is a front side view of another alternative embodiment of the form of FIG. 1.

In another embodiment, illustrated in FIG. 4, the form 100' may consist of a plurality of wristbands 120' and does not include labels 110. Alternately, the form 100" may include only a single wristband 120" as shown in FIG. 5. The form 100 may be approximately the size of a standard piece of paper (e.g., 8½"×11"), or the form 100 may be tailored to the size of the required wristbands 120 and/or labels 110. For example, if only a single wristband 120 is required, the form 100 may be only the size necessary to contain one wristband 120.

Many different arrangements of the described invention are possible without departing from the spirit and scope of the present invention. Embodiments of the present invention are described herein with the intent to be illustrative rather than restrictive. Alternative embodiments will become apparent to those skilled in the art that do not depart from its scope. A skilled artisan may develop alternative means of implementing the disclosed improvements without departing from the scope of the present invention.

Further, it will be understood that certain features and subcombinations are of utility and may be employed without reference to other features and subcombinations and are contemplated within the scope of the claims. Not all steps listed in the various figures and description need to be carried out in the specific order described. The description should not be restricted to the specific described embodiments.

The invention claimed is:

1. A combination wristband and label form, comprising:
   a front ply comprising at least one wristband;
   a back ply, the back ply being at least partially coated in a control bond adhesive, wherein the control bond adhesive is a mixture comprising:
      between about 3 pounds and 4 pounds of a flexible adhesive;
      between about 2 pounds and 3 pounds of soft water;
      between about 1 tsp and 2 tsp gypsum, and
      between about 19 and 22 tsp fumed silica;
   wherein the control bond adhesive maintains the wristband in temporary contact with the back ply.

2. The combination wristband and label form of claim 1, wherein the amount of adhesive is about 3.6 pounds.

3. The combination wristband and label form of claim 2, wherein the amount of soft water is about 2.8 pounds.

4. The combination wristband and label form of claim 3, wherein the amount of gypsum is 1.3 tsp.

5. The combination wristband and label form of claim 4, wherein the amount of fumed silica is about 19 heaping tsp.

6. A combination wristband and label form, comprising:
   a front ply comprising:
      a top portion having a plurality of labels die cut therein; and
      a bottom portion having a generally rectangular wristband configured to receive an indicia, and an outer portion surrounding the wristband; the wristband being separable from the form and being formed of a single ply of water-resistant material; the wristband having a first lateral end and a second lateral end; and
   a back ply, the back ply being at least partially coated in a control bond adhesive and comprising at least one area of silicone, wherein the control bond adhesive is a mixture comprising:
      between about 1 kg and 2 kg of a flexible adhesive;
      between about 1 kg and 2 kg of water;
      between about 12 g and 16 g gypsum, and
      between about 13 g and 23 g fumed silica;
   wherein:
      the control bond adhesive maintains the wristband in temporary contact with the back ply between the first lateral end and the second lateral end;
      removal of the wristband exposes a first area of the back ply, the first area being devoid of a void space; and
      the outer portion is permanently sealed to the back ply.

7. The combination wristband and label form of claim 6, wherein a back side of the top portion of the front ply contains an adhesive, and wherein a corresponding front side of the back ply is coated in a silicone.

8. The combination wristband and label form of claim 6, wherein at least one of the first and second lateral ends is equipped with tamper evident slits.

9. The combination wristband and label form of claim 8, wherein the second lateral end comprises perforations.

10. The combination wristband and label form of claim 9, wherein the first lateral end comprises an adhesive area comprising an adhesive adjacent thereto.

11. The combination wristband and label form of claim 6, wherein the control bond adhesive mixture comprises:
   between about 1.4 kg and 1.8 kg flexible adhesive;
   between about 1.1 kg and 1.3 kg water;
   between about 13 g and 15 g gypsum; and between about 15 g and 22 g fumed silica.

12. The combination wristband and label form of claim 11, wherein the control bond adhesive comprises:
about 1.6 kg flexible adhesive;
about 1.3 kg water;
about 14.87 g gypsum; and
about 16 g fumed silica.

13. The combination wristband and label form of claim 6, wherein the water is soft water.

14. The combination wristband and label form of claim 6, wherein the control bond adhesive is disposed on the back ply in a single layer.

15. The combination wristband and label form of claim 6, wherein the control bond adhesive further comprises an effective amount of pigment.

16. The combination wristband and label form of claim 15, wherein the control bon adhesive is applied to the back ply in a pattern.

17. A method of forming a combination wristband and label form, comprising:
providing a front ply comprising:
a generally rectangular wristband configured to receive an indicia, and an outer portion surrounding the wristband; the wristband being separable from the form and being formed of a single ply of water-resistant material; the wristband having a first lateral end and a second lateral end; and
providing a back ply;
applying a control bond adhesive to the back ply at a first area, the control bond adhesive comprising:
between about 1 kg and 2 kg of a flexible adhesive;
between about 1 kg and 2 kg of water;
between about 12 g and 16 g gypsum, and
between about 13 g and 23 g fumed silica;
applying silicone to the back ply at a second area; and
securing the front ply to the back ply, wherein the wristband mates with the back ply at the first area;
wherein:
the control bond adhesive maintains the wristband in temporary contact with the back ply; and
the outer portion is permanently sealed to the back ply.

18. The method of claim 17, wherein the adhesive comprises about 1.6 kg flexible adhesive, about 1.3 kg soft water, about 14.87 g gypsum, and about 16 g fumed silica.

* * * * *